United States Patent [19]

Ames et al.

[11] Patent Number: 4,497,730

[45] Date of Patent: Feb. 5, 1985

[54] METHOD FOR OBTAINING PERIPLASMIC PROTEINS FROM BACTERIAL CELLS USING CHLOROFORM

[75] Inventors: Giovanna F. Ames, Berkeley; Sydney G. Kustu, Davis, both of Calif.

[73] Assignee: The United States of America as represented by the Department of Health and Human Services, Washington, D.C.

[21] Appl. No.: 596,636

[22] Filed: Apr. 3, 1984

[51] Int. Cl.$^3$ ............................. C07G 7/00; A23J 1/18
[52] U.S. Cl. .................................. 260/112 R; 435/68; 435/879; 426/656
[58] Field of Search .............. 260/112 P; 435/68, 879; 426/656

[56] References Cited

U.S. PATENT DOCUMENTS

| | | | |
|---|---|---|---|
| 3,983,008 | 9/1976 | Shinozaki et al. | 260/112 R X |
| 4,435,386 | 3/1984 | Ribi et al. | 260/112 R X |
| 4,448,714 | 5/1984 | Cunliffe et al. | 260/112 R |
| 4,451,446 | 5/1984 | Vandevelde et al. | 260/112 R X |

OTHER PUBLICATIONS

Nossal and Heppel, J. Biol. Chem., 3055, 1966.
Hogg, J. Bacteriol., 105, 604, 1971.
Ames et al., Biochem., 15: 616, 1976.

*Primary Examiner*—Howard E. Schain
*Attorney, Agent, or Firm*—Holman & Stern

[57] ABSTRACT

The present invention discloses a method of extracting periplasmic protein comprising treating a cellular suspension of an organism possessing said periplasmic proteins with a periplasmic protein releasing volume of chloroform for a sufficient time to release said protein and then separating said protein from said cellular suspension.

4 Claims, 1 Drawing Figure

METHOD FOR OBTAINING PERIPLASMIC PROTEINS FROM BACTERIAL CELLS USING CHLOROFORM

BACKGROUND OF THE INVENTION

1. Field of the Invention

The present invention relates to a method of obtaining proteins from bacterial cells. More particularly, the present invention relates to a method of releasing periplasmic proteins from bacterial cells.

2. The Prior Art

Several methods have been used to release periplasmic proteins from gram-negative bacteria. Treating cells with ethlyenediaminetetraacetate and lysozyme causes the release of periplasmic proteins and the formation of spheroplasts. Another procedure is that of osmotic shock. In this method, bacteria are treated with 40% sucrose, 0.05 molar TRIS-Cl pH 7.8, and 0.002 molar EDTA, followed by cold shock with distilled water.

Solvents have been used to good advantage in permeabilizing and partially lysing bacterial cells. Toluene and phenethyl alcohol have been used to permeabilize cells in order to perform in situ enzyme assays. In order to select for mutants of L-arabinose binding protein, Hogg, J. Bacteriol. 105:604, 1971 used a mixture of chloroform-toluene 1:1 to partially lyse cells on culture plates. However, these prior art methods involve several steps and extensive manipulations which require, inter alia, concentration of cells out of the culture medium, exposing them to buffer solution, then to high concentration of sucrose in the presence of an ion chelator, then again concentrating the cells and suspending them in distilled water and then removing the cells from the final medium, etc. Not only these lengthy manipulative steps are cumbersome but the protein solution so obtained as a final product is also very dilute. This involves a further step of concentrating the dilute protein before it can be used for purification of individual protein components. Such lengthy and unwieldy prior art processes are simply not amenable to large scale screening of periplasmic proteins from multiple batches.

The applicants have now discovered an improved and simple procedure for extracting periplasmic proteins requiring a minimum of manipulations carried out in a comparatively short period of time to obtain a relatively pure periplasmic fraction. An additional advantage of the inventive procedure of the present invention is that it can be used in both small and large scale preparations including fermenter size cultures. Furthermore, prior art osmotic shock process is neither convenient nor efficient for application to a small volume e.g., 2 ml, of cell culture.

SUMMARY OF THE INVENTION

It is, therefore, an object of the present invention to provide a method for releasing proteins from cellular periplasmic space.

It is a further object of the present invention to provide a simple, rapid and effective method for releasing periplasmic proteins from bacteria, more particularly from gram-negative organisms.

Other objects and advantages of the present invention will appear as the description proceeds.

BRIEF DESCRIPTION OF THE DRAWINGS

These and other objects and advantages of the present invention will be better understood upon a reading of the following detailed description when considered in connection with the accompanying FIG. 1 which shows electrophoretograms of periplasmic proteins extracted by the chloroform procedure of the present invention versus conventional osmotic shock process.

DETAILED DESCRIPTION OF THE INVENTION

Figure 1:
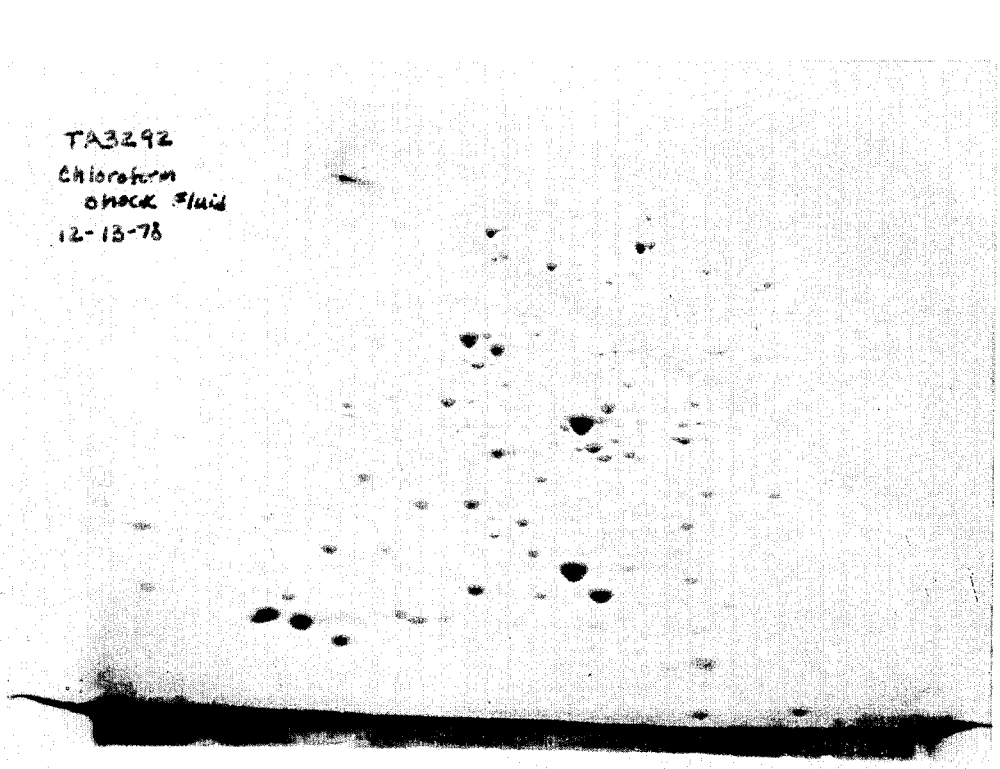
Figure 1:
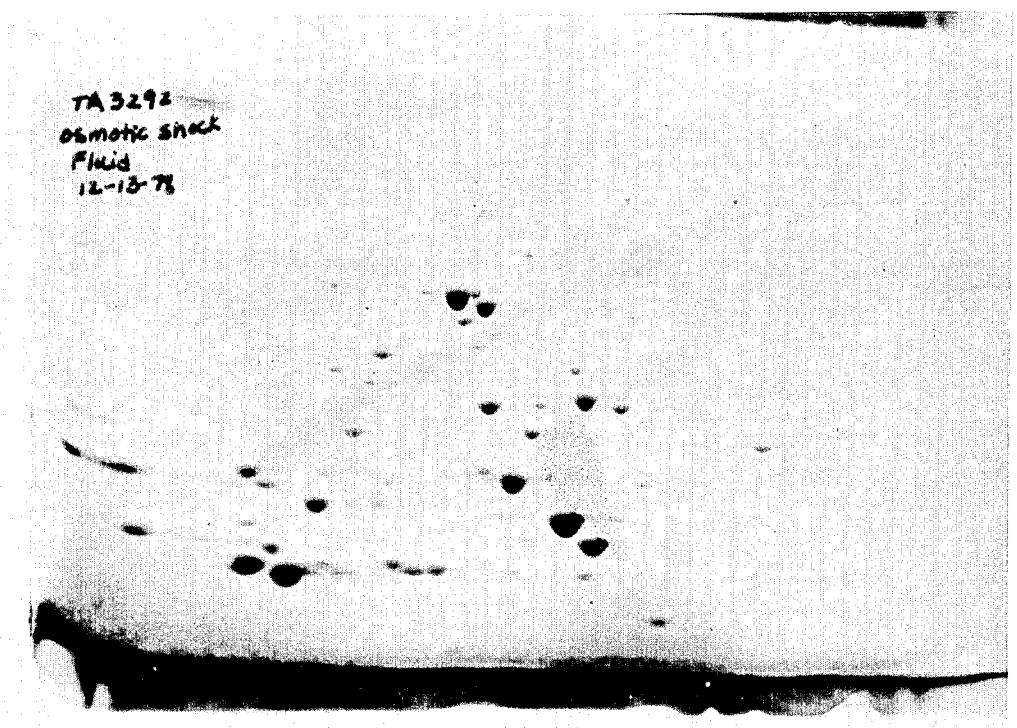

The objects and advantages of the present invention are achieved by a method comprising treating a concentrated bacterial cell suspension to a periplasmic protein releasing volume of chloroform for a sufficient time to release said protein and then separating said protein from said cell suspension. Adding a small amount of TRIS-Cl buffer after exposing the cells to chloroform and prior to separating the proteins is preferred.

The periplasm, of course, is a compartment of gram-negative organisms, such as *Escherichia coli* and *Salmonella typhimurium*, where a special class of proteins is located. Many of the medically and commercially important protein products of recombinant DNA-engineered genes are, or could be, located in the periplasm, e.g. insulin. Release of such proteins effectively, simply, and rapdidly, thus separating them from the rest of the cellular protein, is an essential first step in the large scale production of such proteins.

Although any organism or cells endowed with periplasm, e.g. *Escherichia coli, Salmonella typhimurium*, euglena and the like could be used in the practice of the present invention, *Salmonella typhimurium* strain TA3292 was preferably used in the processes and experiments described herein. Strain TA 2365 was used only where so designated. Strain TA3292 was grown aerobically using standard techniques well known in the art, e.g. Vogel-Bonner minimal medium plus 0.4% glucose at 37° C. A bacterial medium suitable for such purposes is described in Vogel-Bonner, J. Biol. Chem. 218, 97–102, 1956 which is incorporated herein by reference. Of course, other growth media and suitable modifications thereof depending on the type of organism or cells utilized for obtaining periplasmic protein would have to be employed and should be known to those skilled in the art.

The following examples will more fully illustrate the preferred embodiments of the present invention.

EXAMPLE 1

Cell culture of *Salmonella typhimurium* (Strain TA3292), 2 milliliter, grown to stationary phase in Vogel-Bonner minimal medium is centrifuged at about 3,000 rpm in a Sorvall RC-2B centrifuge with SS-34 rotor for about 10 minutes. Supernatant is drawn off with a pasteur pipette and cells are resuspended by vortexing in an amount of the medium that could not be drained off from the tubes (approximately 30 $\mu$l). 10 $\mu$l of chloroform is added to the cells, the tubes are vortexed, and they are allowed to sit at room temperature for about 15 minutes. After 15 minutes, 200 $\mu$l of 0.01 molar TRIS-Cl pH 8.0 is added, and the cells are centrifuged at about 7,000 rpm in the SS-34 rotor for about 20 minutes. Supernatant fluid is drawn off with a pasteur pipette. This supernatant fluid containing the desired proteins can then be subjected to protein assays, gel electrophoresis and other standard purification and isolation techniques etc., as necessary.

EXAMPLE 2

A large scale preparation would require harvesting the cells out of a fermenter by standard methods, e.g. with a Sharples centrifuge, then the cell paste is resuspended to a creamy consistency with a minimal amount of a suitable buffer, e.g. 0.01M TRIS-Cl, pH 7.8 to 8.0, preferably using a waring blender for uniform suspension, then adding suitable amount of chloroform, such amount being determined by the volume of the cell suspension but usually ranging from about 0.1 to 2% of the volume of the cell suspension and stirring the resulting chloroform-cell suspension mixture for a short period of time, upto 30 minutes. The release of periplasmic proteins may be enhanced at this point by adding a minimal amount of said TRIS-Cl buffer in the range of 1 to 10 times the volume of chloroform. The released proteins can now be separated from the cells using standard separation techniques, e.g. centrifugation, filtration and the like.

COMPARATIVE TESTS

In order to show superior results obtained by the method of the present invention over the conventional osmotic shock process of extracting periplasmic proteins, the applicants performed certain comparative studies wherein closely related organic solvents, e.g. toluene and a mixture of toluene and chloroform were also employed. The procedure used was the same as described in Example 1, supra, except that toluene and a mixture of toluene and chloroform was used in place of chloroform. Protein assays were performed either by standard Lowry procedure Lowry, O. H., Rosebrough, N. J., Farr, A. L. and Randall, R. J. J. Biol. Chem. 193:265, (1951) and/or by standard sodium dodecyl sulfate (SDS) gel electrophoresis. Osmotic shock treatment was performed as described by Neu et al, J. Biol. Chem. 240:3685, 1965 which is incorporated herein by reference. The results are presented below.

| Treatment | Mg. Protein Released | |
|---|---|---|
| | Expt 1 | Expt 2 |
| Chloroform | 0.118 | 0.109 |
| Chloroform-Toluene 9:1 | 0.107 | 0.079 |
| Chloroform-Toluene 1:1 | 0.102 | 0.052 |
| Chloroform-Toluene 1:9 | 0.093 | 0.048 |
| Toluene | 0.083 | 0.053 |
| Osmotic Shock | 0.037 | 0.037 |

Qualitative results obtained by two dimensional SDS gel electrophoresis showed that the proteins released by treating with chloroform alone were the same as obtained by conventional osmotic shock method. FIG. 1 shows the comparative results of such an electrophoresis. The electrophoresis was performed in accordance with the technique described by Ames et al, Biochem., 15:616 (1976) which is incorporated herein by reference.

These data clearly demonstrate the unexpected results of the present invention over the known method of obtaining periplasmic proteins.

It is understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method of extracting periplasmic protein comprising treating without homogenizing a cellular suspension of an organism possessing said periplasmic protein with a periplasmic protein releasing volume only of chloroform as an organic solvent for a sufficient time to release said protein and then separating said protein from said cellular suspension.

2. The method of claim 1 wherein said organism is gram-negative bacteria.

3. The method of claim 2 wherein said gram-negative bacteria is *Escherichia coli* or *Salmonella typhimurium*.

4. The method of claim 1 additionally comprising adding 0.01M TRIS-Cl buffer, pH 7.8 to 8 after the chloroform treatment step in an amount ranging from about 1 to 20 times the volume of chloroform.

* * * * *